United States Patent [19]

Holt

[11] Patent Number: 5,009,226
[45] Date of Patent: Apr. 23, 1991

[54] MECHANICAL RESUSCITATOR

[76] Inventor: William T. Holt, 4610 Ellendale Rd., Memphis, Tenn. 38135

[21] Appl. No.: 523,897

[22] Filed: May 14, 1990

[51] Int. Cl.⁵ .............................................. A62B 7/00
[52] U.S. Cl. ............................ 128/205.18; 128/205.13
[58] Field of Search ..................... 128/205.13, 205.14, 128/205.18, 202.28, 202.29, 203.11

[56] References Cited

U.S. PATENT DOCUMENTS

| | | | |
|---|---|---|---|
| 1,172,879 | 2/1916 | Davis | 128/205.18 |
| 1,197,232 | 9/1916 | Pierpont | |
| 1,201,092 | 10/1916 | Phillips | 128/205.18 |
| 1,202,125 | 10/1916 | Tullar | 128/205.13 |
| 1,371,702 | 3/1921 | Lyon | |
| 1,406,141 | 2/1922 | Anston | |
| 2,427,419 | 9/1947 | Rausch | 128/29 |
| 2,428,451 | 10/1947 | Emerson | 128/29 |
| 3,283,754 | 11/1966 | Goodner | 128/205.14 |
| 3,461,866 | 8/1969 | Ritchie | 128/145.7 |
| 4,077,404 | 3/1978 | Elam | 128/145.8 |
| 4,239,038 | 12/1980 | Holmes | 128/205.13 |
| 4,870,962 | 10/1989 | Sitnik | 128/205.13 |
| 4,898,166 | 2/1990 | Rose et al. | 128/205.13 |

Primary Examiner—Aaron J. Lewis
Attorney, Agent, or Firm—Walker & McKenzie

[57] ABSTRACT

A resuscitator for conveying gas to a patient's lungs. The resuscitator includes a pump having a cavity and including movable structure movable between a first position and a second position for forcing gas from the cavity of the pump when moved from the first position to the second position and for drawing gas into the cavity of the pump when moved from the second position to the first position, the pump having an opening for allowing gas to be drawn into and forced out of the cavity thereof; a base member having a passageway for allowing gas to pass therethrough, the passageway having a first end and a second end; coupling structure for allowing gas to pass from the passageway of the base member to the patient's lungs, the coupling structure including a hollow tube for being connected to the second end of the passageway of the base member to allow gas to pass from the passageway of the base member therethrough; and seal structure for forming a gas-tight seal between the opening of the pump and the first end of the passageway of the base member when the movable structure of the pump is moved from the first position to the second position to allow gas to be forced from the cavity of the pump through the passageway of the base member and out the coupling structure.

19 Claims, 2 Drawing Sheets

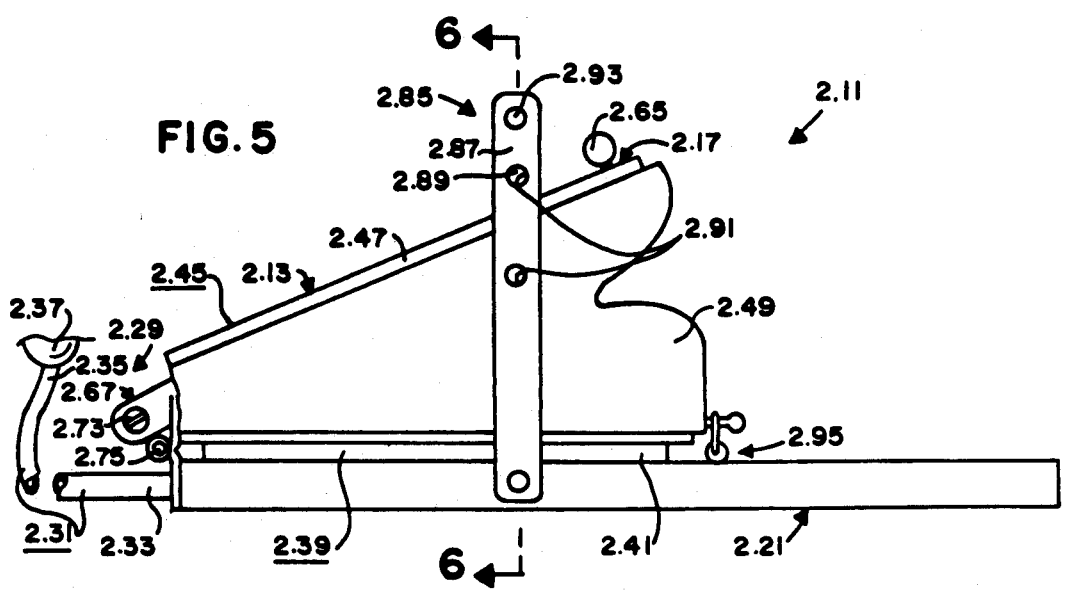
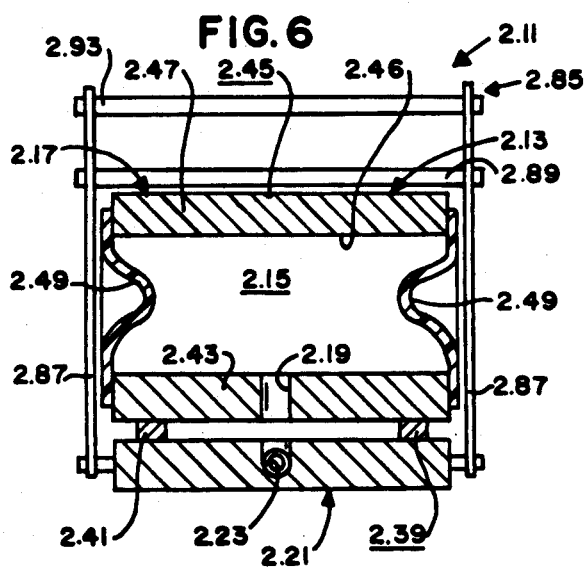
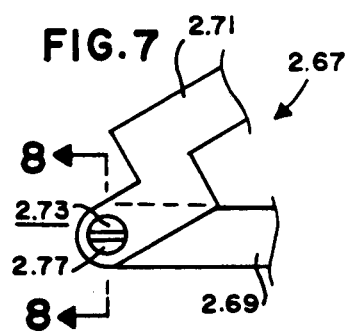
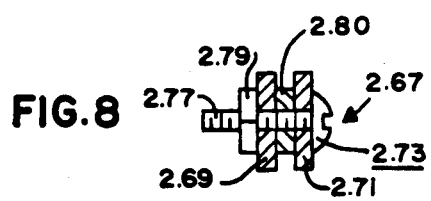
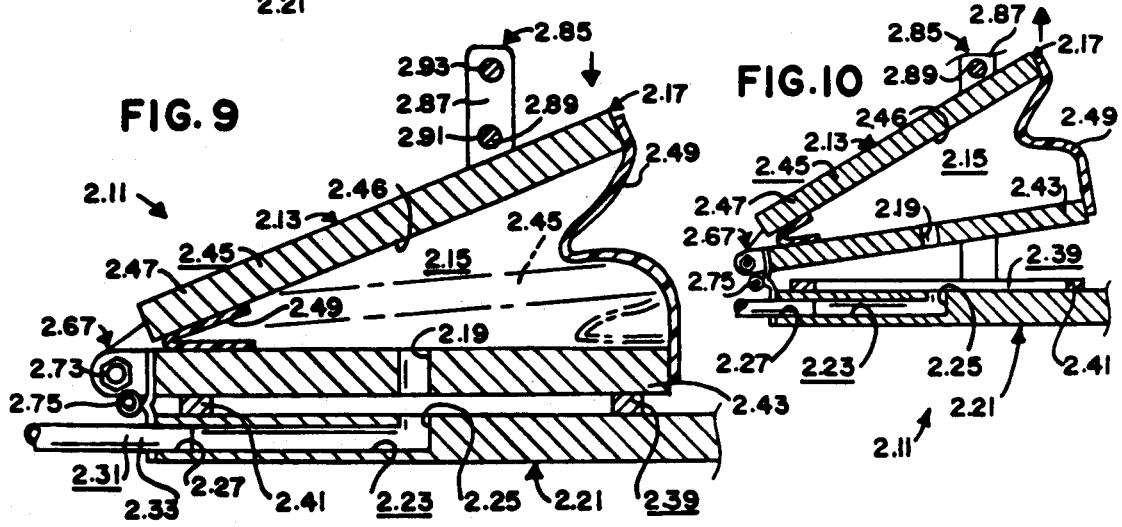

MECHANICAL RESUSCITATOR

BACKGROUND OF THE INVENTION

1. Field of the Invention

The present invention relates, in general, to resuscitators for assisting or reestablishing the breathing of a patient.

2. Information Disclosure Statement

A preliminary patentability search conducted in class 128, subclasses 205.13 and 205.18 produced the following patents: Pierpont, U.S. Pat. No. 1,197,232; Lyon, U.S. Pat. No. 1,371,702; Anston, U.S. Pat. No. 1,406,141; Rausch, U.S. Pat. No. 2,427,419; Emerson, U.S. Pat. No. 2,428,451; Ritchie, U.S. Pat. No. 3,461,866; Elam, U.S. Pat. No. 4,077,404; Holmes, U.S. Pat. No. 4,239,038; Sitnik, U.S. Pat. No. 4,870,962.

Pierpont discloses a device including a hand operated bellows having first and second chambers. When the bellows is operated, positive pressure is created in the first chamber to force oxygen or atmospheric air into a patient's lungs and a vacuum is created in the second chamber to draw vitiated air out of the patient's lungs.

Lyon discloses a device including a hand operated piston coupled to a face mask by first and second conduits. When the piston is operated, positive pressure is created on the downstroke to force air into a patient's lungs and negative pressure is created on the upstroke to draw air from the patient's lungs. Structure is provided to allow the volume of air pumped per pump stroke to be varied.

Anston discloses an apparatus for first drawing impure air out of a patient's body, forcing clean air into the patient's body, and then causing a constant circulation of air for a sufficient time to insure exercise and full expansion of the patient's lungs and bronchial tubes.

Rausch discloses a resuscitating apparatus for forcing gas into a patient's lungs and for exhausting the spent gas from the patient's lungs by suction. The apparatus includes structure for maintaining the positive and negative pressures created thereby within certain limits.

Emerson discloses a pressure resuscitator which intermittently forces air or oxygen into a patient's lungs so as to inflate the lungs, the deflation of the lungs depending upon the elasticity thereof.

Ritchie discloses a respirator including a pair of piston-type pumps connected by a piston rod to a common handle for simultaneous reciprocal operation. One pump is operable on one stroke of the handle to induce inhalation by a patient and the other pump is operable on the other stroke of the handle to induce exhalation by the patient. Valves are provided to prevent excess positive or negative pressures.

Elam discloses a resuscitator valve mechanism having inspiration and expiration ports, and arranged to assure automatic operation to effect oxygen "blow-by" under conditions of operation tending to close the expiration port to thereby prevent undesirable build-up of pressure in the patient's lungs.

Holmes discloses a manually operable resuscitator having a reservoir into which breathable gas is drawn and from which the gas may be directed to a patient, and having a valve assembly which prevents exhaled gas from returning to the reservoir and which keeps the space in which the exhaled gas is retained small to ensure that the subsequent inhalation gases to the patient include only a small proportion of carbon dioxide.

Sitnik discloses a disposable self-inflating manual resuscitator bag that is shaped like a pleated, handleless bellows where the pleats act like a spring following compression to rapidly re-inflate the bag to its fully recovered state.

None of the above patents disclose or suggest the present invention. More specifically, none of the above patents disclose or suggest a resuscitator including a pump having a cavity and including movable means movable between a first position and a second position for forcing gas from the cavity of the pump when moved from the first position to the second position and for drawing gas into the cavity of the pump when moved from the second position to the first position, the pump having an opening for allowing gas to be drawn into and forced out of the cavity thereof; a base member having a passageway for allowing gas to pass therethrough, the passageway having a first end and a second end; coupling means for allowing gas to pass from the passageway of the base member to the patient's lungs, the coupling means including a hollow tube for being connected to the second end of the passageway of the base member to allow gas to pass from the passageway of the base member therethrough; and seal means for forming a gas-tight seal between the opening of the pump and the first end of the passageway of the base member when the movable means of the pump is moved from the first position to the second position to allow gas to be forced from the cavity of the pump through the passageway of the base member and out the coupling means.

SUMMARY OF THE INVENTION

The present invention is directed toward providing an improved resuscitator for conveying gas to a patient's lungs to assist or re-establish the breathing of the patient.

The resuscitator of the present invention includes a pump having a cavity and including movable means movable between a first position and a second position for forcing gas from the cavity of the pump when moved from the first position to the second position and for drawing gas into the cavity of the pump when moved from the second position to the first position, the pump having an opening for allowing gas to be drawn into and forced out of the cavity thereof; a base member having a passageway for allowing gas to pass therethrough, the passageway having a first end and a second end; coupling means for allowing gas to pass from the passageway of the base member to the patient's lungs, the coupling means including a hollow tube for being connected to the second end of the passageway of the base member to allow gas to pass from the passageway of the base member therethrough; and seal means for forming a gas-tight seal between the opening of the pump and the first end of the passageway of the base member when the movable means of the pump is moved from the first position to the second position to allow gas to be forced from the cavity of the pump through the passageway of the base member and out the coupling means.

BRIEF DESCRIPTION OF THE DRAWINGS

FIG. 5 is a side elevational view of a second embodiment of the resuscitator of the present invention with portions thereof broken away for clarity.

FIG. 6 is a sectional view substantially as taken on line 6—6 of FIG. 5.

FIG. 7 is an enlarged side elevational view of a portion of FIG. 5.

FIG. 8 is a sectional view substantially as taken on line 8—8 of FIG. 7.

FIG. 9 is a sectional view substantially as taken on line 9—9 of FIG. 6.

FIG. 10 is a sectional view similar to FIG. 9 but reduced in size and with portions of the resuscitator shown in a moved position.

DESCRIPTION OF THE PREFERRED EMBODIMENT

The resuscitator of the present invention is used to convey gas to a patient's lungs. More specifically, the resuscitator of the present invention is a manually operated device used to assist or re-establish the breathing of a patient.

A first preferred embodiment of the resuscitator is shown in FIGS. 1-4 and is identified by the numeral 11.

Figure 2:
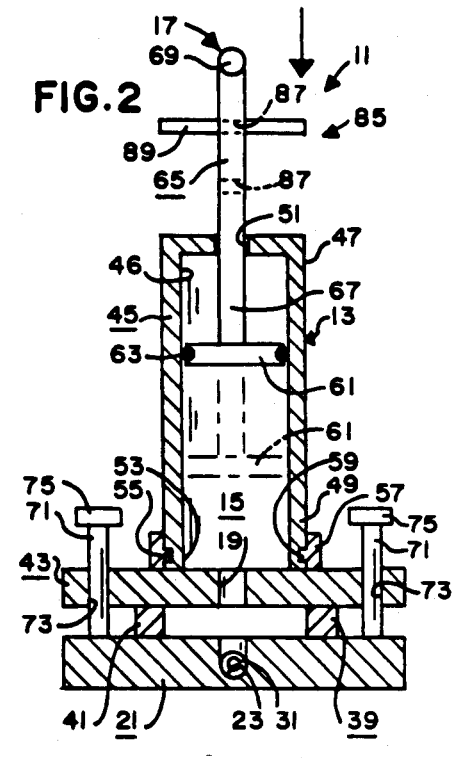
FIG. 2 is a sectional view substantially as taken on line 2—2 of FIG. 1.

The resuscitator 11 includes a pump 13 having a cavity 15 and including movable means 17 movable between a first position as shown in solid lines in FIG. 2 and a second position as shown in broken lines in FIG. 2 for forcing gas from the cavity 15 of the pump 13 when moved from the first position to the second position and for drawing gas into the cavity 15 of the pump 13 when moved from the second position to the first position. The pump 13 has an opening 19 for allowing gas to be drawn into and forced out of the cavity 15 thereof (see FIG. 2).

The resuscitator 11 includes a base member 21 having a passageway 23 for allowing gas to pass therethrough. The passageway 23 has a first end 25 and a second end 27.

The resuscitator 11 includes coupling means 29 for allowing gas to pass from the passageway 23 of the base member 21 to the patient's lungs. The coupling means 29 includes a hollow tube 31 for being connected to the second end 27 of the passageway 23 of the base member 21 to allow gas to pass from the passageway 23 of the base member 21 therethrough. Thus, the tube 31 preferably includes a first end 33 for being attached to the second end 27 of the passageway 23 of the base member 21 and a second end 35 for being applied to the patient in a known manner. For example, the second end 35 of the tube 31 may form or be attached to a face mask 37 for being positioned over the patient's mouth and nose, etc., as will now be apparent to those skilled in the art.

The resuscitator 11 includes seal means 39 for forming a gas-tight seal between the opening 19 of the pump 13 and the first end 25 of the passageway 23 of the base member 21 when the movable means 17 of the pump is moved from the first position to the second position to allow gas to be forced from the cavity 15 of the pump 13 through the passageway 23 of the base member 21 and out the coupling means 29. The seal means 39 preferably includes a seal member 41 surrounding the first end 25 of the passageway 23 of the base member 21. The seal member 41 is preferably resilient. More specifically, the seal member 41 preferably consists of a rubber O-ring or the like mounted on the base member 21 in a position surrounding the first end 25 of the passageway 23 to form a gas-tight seal between the opening 19 of the pump 13 and the first end 25 of the passageway 23. More specifically, the pump 13 preferably includes a plate member 43 for being forced against the seal member 41 when the movable means 17 thereof is moved from the first position to the second position to thereby cause the seal member 41 to form a gas-tight seal between the plate member 43 (hereinafter referred to as the seal plate member 43) and the base member 21 as will now be apparent to those skilled in the art. The opening 19 of the pump 13 preferably extends through the seal plate member 43 thereof and substantially aligns with the first end 25 of the passageway 23 of the base member 21 and is surrounded by the seal member 41 when the movable means 17 of the pump 13 is moved from the first position to the second position to thereby cause a gas-tight seal to be formed between the opening 19 and passageway 23 as will now be apparent to those skilled in the art. The seal plate member 43 of the pump 13 is moved away from the seal member 41 of the seal means 39 when the movable means 17 of the pump 13 is moved from the second position to the first position as clearly shown in FIG. 4 to break the gas-tight seal between the opening 19 and passageway 23.

The pump 13 preferably includes a piston cylinder-type body member 45. The body member 45 preferably has a hollow interior or chamber 46 that defines or forms the cavity 15 of the pump 13. The body member 45 has a first end 47 and a second end 49. The second end 49 of the body member 45 is preferably removably attached to the seal plate member 43 with the opening 19 through the seal plate member 43 aligned with and communicating with the chamber 46. The body member 45 preferably consists of an elongated, hollow cylinder having a central aperture 51 through its first end 47. The second end 49 of the body member 45 is preferably completely open to form a mouth 53. Threads 55 or the like are preferably provided on the second end 49 and the seal plate member 43 preferably includes a boss member 57 or the like having threads 59 to allow the body member 45 to be removably attached to the seal plate member 43 as will now be apparent to those skilled in the art.

The movable means 17 of the pump 13 preferably includes a piston 61 reciprocatingly mounted in chamber 46 of the body member 45. A gas-tight seal is preferably formed between the piston 61 and the side of the chamber 46 so that reciprocating movement of the piston 61 within the chamber 46 will cause gas to be pumped through the opening 19 as will now be apparent to those skilled in the art. Thus, the piston 61 may include a seal 63 such as a typical O-ring for forming a gas-tight seal between the piston 61 and the side of the chamber 46 as clearly shown in FIGS. 2 and 4 and as will now be apparent to those skilled in the art.

The movable means 17 of the pump 13 preferably includes a handle 65 coupled to the piston 61 for moving the piston 61 between first and second positions. The handle 65 preferably has a first end 67 fixedly attached to the piston 61 and a second end 69 extending through the central aperture 51 in the first end 47 of the body member 45. The second end 69 of the handle 65 is preferably T-shaped as shown in FIG. 1 to allow easy manual use thereof as will now be apparent to those skilled in the art.

Figure 1:
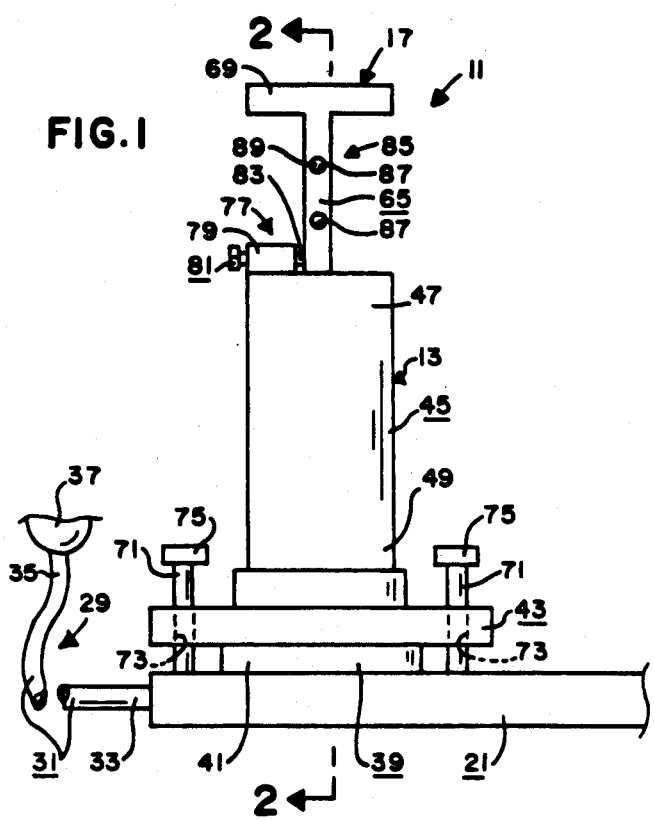
FIG. 1 is a side elevational view of a first embodiment of the resuscitator of the present invention with portions thereof broken away for clarity.
Figure 3:
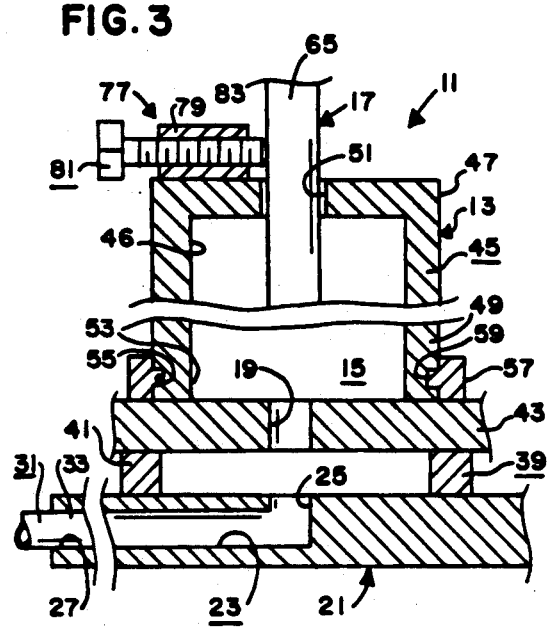
FIG. 3 is an enlarged sectional view of a portion of FIG. 1.
Figure 4:
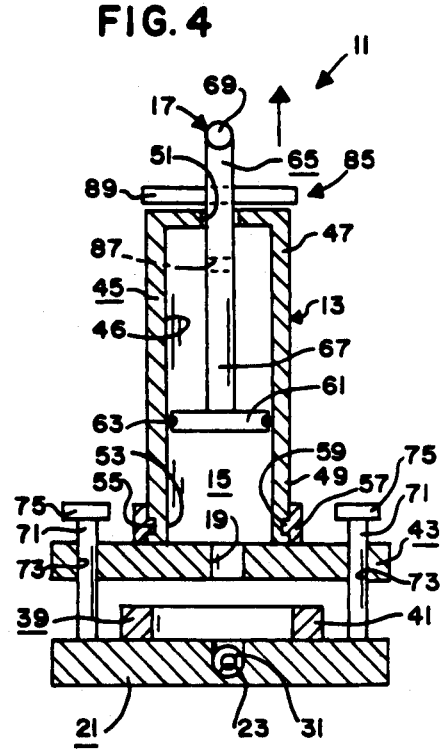
FIG. 4 is a sectional view similar to FIG. 2 but with portions of the resuscitator shown in a moved position.

A plurality of upstanding posts 71 are preferably mounted on the base member 21 for extending through apertures 73 in the seal plate member 43 to slidably mount the pump 13 to the base member 21 for allowing the pump 13 to be moved between a first position with the seal plate member 43 pressed against the seal member 41 as shown in FIGS. 1, 2 and 3 to form a gas-tight seal between the seal plate member 43 and the base member 21, and a second position with the seal plate member 43 spaced from the seal member 41 as shown in FIG. 4 to allow gas to pass therebetween. The posts 71 preferably include enlarged head portions 75 to act as stops and to prevent the pump 13 from being accidently removed therefrom as will now be apparent to those skilled in the art.

The resuscitator 11 preferably includes adjustment means for adjusting the pressure the seal plate member 43 of the pump ;3 exerts against the seal member 41 when the movable means 17 of the pump 13 is moved from the first position to the second position. The adjustment means preferably adjusts the amount of pressure required to move the movable means 17 of the pump 13 between the first and second positions. The adjustment means preferably includes screw means 77 coupled to the body member 45 of the pump 13 for adjustably engaging the handle 65 of the pump 13 and for adjusting the friction between the body member 45 of the pump 13 and the handle 65 of the pump 13. More specifically, the screw means 77 preferably includes an internally threaded body 79 fixedly attached to the first end 47 of the body member 45 and an externally threaded screw 81 extending through the body 79 as clearly shown in FIG. 3. The screw 81 has a distal end 83 for engaging the exterior surface of the handle 65 so that the pressure required to move the movable means 17 of the pump 13 between the first and second positions can be increased by merely tightening the screw 81 as will now be apparent to those skilled in the art. Increasing the pressure required to move the movable means 17 of the pump 13 from the first position to the second position will increase the pressure the seal plate member 43 of the pump 13 exerts against the seal member 41 and will thus increase the "seal" between the base member 21 and seal plate member 43 as will now be apparent to those skilled in the art.

The resuscitator 11 preferably includes control means for controlling the amount of gas forced from the cavity 15 of the pump 13 when the movable means 17 is moved from the first position to the second position. The control means preferably includes limit means 85 for limiting the travel of the piston 61 in the chamber 46 of the body member 45 of the pump 13 to thereby limit the effective volume of the chamber 46. The handle 65 of the pump 13 preferably has a plurality of spaced apart transverse apertures 87 therethrough and the limit means 85 preferably includes a rod member 89 for being inserted into one of the spaced apart transverse apertures 87 through the handle 65 and for engaging the first end 47 of the body member 45 when the movable means 17 is moved to the second position to act as a stop as clearly shown in FIG. 4. By moving the rod member 89 between the spaced apart transverse apertures 87, the amount of travel the piston 61 is allowed will be varied to thereby vary the amount of gas that is forced from the cavity 15 of the pump 13 when the movable means 17 is moved from the first position to the second position as will now be apparent to those skilled in the art.

A second preferred embodiment of the resuscitator is shown in FIGS. 5–9 and is identified by the numeral 2.11.

The resuscitator 2.11 includes a pump 2.13 having a cavity 2.15 and including movable means 2.17 movable between a first position as shown in solid lines in FIGS. 5, 6, and 9 and a second position as shown in broken lines in FIG. 9 for forcing gas from the cavity 2.15 of the pump 2.13 when moved from the first position to the second position and for drawing gas into the cavity 2.15 of the pump 2.13 when moved from the second position to the first position. The pump 2.13 has an opening 2.19 for allowing gas to be drawn into and forced out of the cavity 15 thereof (see FIG. 2).

The resuscitator 2.11 includes a base member 2.21 having a passageway 2.23 for allowing gas to pass therethrough. The passageway 2.23 has a first end 2.25 and a second end 2.27.

The resuscitator 2.11 includes coupling means 2.29 for allowing gas to pass from the passageway 2.23 of the base member 2.21 to the patient's lungs. The coupling means 2.29 preferably includes a hollow tube 2.31 for being connected to the second end 2.27 of the passageway 2.23 of the base member 2.21 to allow gas to pass from the passageway 2.23 of the base member 2.21 therethrough. Thus, the tube 2.31 preferably includes a first end 2.33 for being attached to the second end 2.27 of the passageway 2.23 of the base member 2.21 and a second end 2.35 for being applied to the patient in a known manner. For example, the second end 2.35 of the tube 2.31 may form or be attached to a face mask 2.37 for being positioned over the patient's mouth and nose, etc., as will now be apparent to those skilled in the art.

The resuscitator 2.11 includes seal means 2.39 for forming a gas-tight seal between the opening 2.19 of the pump 2.13 and the first end 2.25 of the passageway 2.23 of the base member 2.21 when the movable means 2.17 of the pump is moved from the first position to the second position to allow gas to be forced from the cavity 2.15 of the pump 2.13 through the passageway 2.23 of the base member 2.21 and out the coupling means 2.29. The seal means 2.39 preferably includes a seal member 2.41 surrounding the first end 2.25 of the passageway 2.23 of the base member 2.21. The seal member 2.41 is preferably resilient. More specifically, the seal member 2.41 preferably consists of a rubber O-ring or the like mounted on the base member 2.21 in a position surrounding the first end 2.25 of the passageway 2.23 to form a gas-tight seal between the opening 2.19 of the pump 2.13 and the first end 2.25 of the passageway 2.23. More specifically, the pump 2.13 preferably includes a plate member 2.43 for being forced against the seal member 2.41 when the movable means 2.17 thereof is moved from the first position to the second position to thereby cause the seal member 2.41 to form a gas-tight seal between the plate member 2.43 (hereinafter referred to as the seal plate member 2.43) and the base member 2.21 as will now be apparent to those skilled in the art. The opening 2.19 of the pump 2.13 preferably extends through the seal plate member 2.43 thereof and substantially aligns with the first end 2.25 of the passageway 2.23 of the base member 2.21 and is surrounded by the seal member 2.41 when the movable means 2.17 of the pump 2.13 is moved from the first position to the second position to thereby cause a gas-tight seal to be formed between the opening 2.19 and passageway 2.23 as will now be apparent to those skilled in the art. The seal plate member 2.43 of the pump 13 is moved away from the seal member 2.41 of the seal means 2.39 as shown in FIG. 10 when the movable means 2.17 of the pump 13 is moved from the second position to the first position to break the gas-tight seal between the opening 2.19 and passageway 2.23.

The pump 13 preferably includes a bellows-type body member 2.45. The body member 2.45 preferably has a hollow interior or chamber 2.46 that defines or forms the cavity 2.15 of the pump 2.13. The body member 2.45 preferably includes a movable plate member 2.47 and gas-impermeable flexible means 2.49 for joining the movable plate member 2.47 to the seal plate member 2.43 in an accordion or bellows like manner to form the chamber 2.46 therebetween. The edges of the flexible means 2.49 is attached to the plate members 2.43, 2.47 in a substantially gas-tight manner by glue or the like to completely close the chamber 2.46 with the exception of the opening 2.19 so that gas will be pumped in and out the opening 2.19 when the plate member 2.47 is moved toward and away from the plate member 2.43 as will now be apparent to those skilled in the art.

The movable means 2.17 of the pump 2.13 preferably includes a knob or handle 2.65 attached to the movable plate member 2.47 for use in moving the movable plate member 2.47 toward and away from the seal plate member 2.43. Hinge means 2.67 are preferably provided for hingeably attaching one end of the seal plate member 2.43 to one end of the movable plate member 2.47. The hinge means 2.67 preferably includes a first arm 2.69 for being fixedly attached to the seal plate member 2.43 by screws or the like (not shown), a second arm 2.71 for being fixedly attached to the movable plate member 2.47 by screws or the like (not shown), and pivot means 2.73 for pivotally joining the first and second arms 2.69, 2.71 to one another as will now be apparent to those skilled in the art.

The resuscitator 2.11 preferably includes hinge means 2.75 for movably mounting the pump 2.13 to the base member 2.21 for allowing the pump 2.13 to be moved between a first position with the seal plate member 2.43 pressed against the seal member 2.41 as shown in FIGS. 5, 6 and 9 to form a gas-tight seal between the seal plate member 2.43 and the base member 2.21, and a second position with the seal plate member 2.43 spaced from the seal member 2.41 as shown in FIG. 10 to allow gas to pass therebetween. The hinge means 2.75 may consist of one or more typical piano-type hinges with one leaf fixedly attached to one end of the base member 2.21 with screws or the like (not shown), with another leaf fixedly attached to one end of the seal plate member 2.43 with screws or the like (not shown), and with pivot means pivotally joining the two leaves to one another as will now be apparent to those skilled in the art.

The resuscitator 2.11 preferably includes adjustment means for adjusting the pressure the seal plate member 2.43 of the pump 2.13 exerts against the seal member 2.41 when the movable means 2.17 of the pump 2.13 is moved from the first position to the second position. The adjustment means preferably adjusts the amount of pressure required to move the movable means 2.17 of the pump 2.13 between the first and second positions. The adjustment means preferably includes means for adjusting the friction between the seal plate member 2.43 and the movable plate member 2.47. More specifically, the adjustment means preferably includes means for adjusting the rotational friction of the pivot means 2.73. Thus, the pivot means 2.73 preferably includes a screw 2.77, a coacting nut 2.79, and a coacting friction washer 2.80 that can be tightened or loosened to vary the pressure required to move the movable plate member 2.47 toward and away from the seal plate member 2.43 by merely tightening or loosening the screw 2.77 to increase the friction between the first and second arms 2.69, 2.71 of the hinge means 2.67 as will now be apparent to those skilled in the art. Increasing the pressure required to move the movable means 2.17 of the pump 2.13 from the first position to the second position will increase the pressure the seal plate member 2.43 of the pump 2.13 exerts against the seal member 2.41 and will thus increase the "seal" between the base member 2.21 and seal plate member 2.43 as will now be apparent to those skilled in the art.

The resuscitator 2.11 preferably includes control means for controlling the amount of gas forced from the cavity 2.15 of the pump 2.13 when the movable means 2.17 is moved from the first position to the second position. The control means preferably includes limit means 2.85 for limiting the travel of the movable plate member 2.47 with respect to the seal plate member 2.43 to thereby limit the effective volume of the chamber 2.46. The limit means 2.85 preferably includes a pair of leg members 2.87 attached to and extending upwardly from the base member 2.21, and a cross member 2.89 for extending between the leg members 2.87 to act as a stop for the movable plate member 2.47 as clearly shown in FIG. 6 and thereby limit the effective volume of the chamber 2.46 as will now be apparent to those skilled in the art. Each leg member 2.87 preferably has a plurality of spaced apart apertures 2.91 for receiving the cross member 2.89 to allow the amount of travel by the movable plate member 2.47 to be varied to thereby vary the amount of gas that is forced from the cavity 2.15 of the pump 2.13 when the movable means 2.17 is moved from the first position to the second position as will now be apparent to those skilled in the art. A fixed cross member 2.93 is preferably attached to the upper ends of the leg members 2.87 to strengthen the unit and define the maximum movement of the movable plate member 2.47.

Lock means 2.95 may be provided between the movable plate member 2.47 and the base member 2.21 (see FIG. 5) to selectively lock the movable plate member 2.47 to the base member 2.21 for travel, etc. The lock means 2.95 may consist of a typical hook-and-eye type lock as will now be apparent to those skilled in the art.

To use any embodiment of the resuscitator of the present invention, the patient is typically placed supine on a support surface (e.g., the ground) and the face mask is placed over the patient's mouth. The pump can then be activated to convey gas to the patient's lungs as will now be apparent to those skilled in the art. It should be noted that the resuscitator of the present invention may be placed on the patient's chest so that when the pump is activated by applying up and down pressure thereto, up and down pressure will be applied to the patient's chest to enhance the resuscitation effort.

Although the present invention has been described and illustrated with respect to preferred embodiments and a preferred use therefor, it is not to be so limited since modifications and changes can be made therein which are within the full intended scope of the invention.

I claim:

1. A resuscitator for conveying gas to a patient's lungs, said resuscitator comprising:
   (a) a pump having a cavity and including movable means movable between a first position and a second position for forcing gas from said cavity of said pump when moved from said first position to said second position and for drawing gas into said cavity of said pump when moved from said second position to said first position, said pump having an opening for allowing gas to be drawn into and forced out of said cavity thereof;

(b) a base member having a passageway for allowing gas to pass therethrough, said passageway having a first end and a second end;

(c) coupling means for allowing gas to pass from said passageway of said base member to said patient's lungs, said coupling means including a hollow tube for being connected to said second end of said passageway of said base member to allow gas to pass from said passageway of said base member therethrough; and (d) seal means for forming a gas-tight seal between said opening of said pump and said first end of said passageway of said base member when said movable means of said pump is moved from said first position to said second position to allow gas to be forced from said cavity of said pump through said passageway of said base member and out said coupling means.

2. The resuscitator of claim 1 in which said seal means includes a seal member surrounding said first end of said passageway of said base member; and in which said pump includes a seal plate member for being forced against said seal member when said movable means thereof is moved from said first position to said second position.

3. The resuscitator of claim 2 in which said seal plate member of said pump is moved away from said seal member of said seal means when said movable means of said pump is moved from said second position to said first position.

4. The resuscitator of claim 3 in which said opening of said pump extends through said seal plate member thereof and substantially aligns with said first end of said passageway of said base member and is surrounded by said seal member when said movable means of said pump is moved from said first position to said second position.

5. The resuscitator of claim 4 in which said seal member is resilient.

6. The resuscitator of claim 4 in which is included adjustment means for adjusting the pressure said seal plate member of said pump exerts against said seal member when said movable means of said pump is moved from said first position to said second position.

7. The resuscitator of claim 6 in which said adjustment means adjusts the amount of pressure required to move said movable means of said pump between said first and second positions.

8. The resuscitator of claim 7 in which is included control means for controlling the amount of gas forced from said cavity of said pump when said movable means is moved from said first position to said second position.

9. The resuscitator of claim 8 in which said pump includes a body member, said body member having a chamber for forming said cavity of said pump, said body member being attached to said seal plate member with said opening through said seal plate member communicating with said chamber of said body member; and in which said movable means of said pump includes a piston reciprocatingly mounted in said chamber of said body member.

10. The resuscitator of claim 9 in which said movable means of said pump includes a handle coupled to said piston for moving said piston between first and second positions.

11. The resuscitator of claim 10 in which said adjustment means includes screw means coupled to said body member of said pump for adjustably engaging said handle of said pump and for adjusting the friction between said body member of said pump and said handle of said pump.

12. The resuscitator of claim 11 in which said control means includes limit means for limiting the travel of said piston in said chamber of said body member of said pump.

13. The resuscitator of claim 12 in which said handle has a plurality of spaced apart transverse apertures therethrough; and in which said limit means of said control means includes a rod member for being inserted into one of said spaced apart transverse apertures through said handle.

14. The resuscitator of claim 8 in which said movable means of said pump includes a bellows-type body member; said bellows-type body member includes a movable plate member and a gas-impermeable flexible means for joining said movable plate member to said seal plate member.

15. The resuscitator of claim 14 in which is included hinge means for hingeably attaching one end of said seal plate member to one end of said movable plate member.

16. The resuscitator of claim 15 in which is included hinge means for hingeably attaching said pump to said base member.

17. The resuscitator of claim 16 in which said control means includes limit means for limiting the travel of said movable plate member from said seal plate member.

18. The resuscitator of claim 17 in which said limit means includes a pair of leg members attached to and extending upwardly from said base member, and a cross member for extending between said leg members to act as a stop for said movable plate member.

19. The resuscitator of claim 15 in which said adjustment means includes means for adjusting the rotational friction of said hinge means for hingeably attaching one end of said seal plate member to one end of said movable plate member.

* * * * *